United States Patent [19]

Nishida et al.

[11] Patent Number: 5,572,439
[45] Date of Patent: Nov. 5, 1996

[54] MOLECULAR DESIGN SUPPORT SYSTEM

[75] Inventors: Kazuhiro Nishida, Kawasaki; Takaaki Harada, Chikushino, both of Japan

[73] Assignee: Fujitsu Limited, Kawasaki, Japan

[21] Appl. No.: 446,300

[22] Filed: May 22, 1996

Related U.S. Application Data

[63] Continuation of Ser. No. 993,775, Dec. 21, 1992, abandoned.

[30] Foreign Application Priority Data

Dec. 20, 1991 [JP] Japan ................................. 3-338878

[51] Int. Cl.$^6$ ............................ G06F 17/50; G06F 19/00
[52] U.S. Cl. .......................................... 364/496; 364/578
[58] Field of Search .................... 364/496, 497, 364/499, 578, 223.4, 924.3; 395/919, 920, 119; 436/89, 508; 434/298

[56] References Cited

U.S. PATENT DOCUMENTS

| | | | |
|---|---|---|---|
| 4,982,338 | 1/1991 | Fujita | 364/496 X |
| 5,157,736 | 10/1992 | Boyer et al. | 364/496 X |
| 5,237,647 | 8/1993 | Roberts et al. | 395/119 |
| 5,249,137 | 9/1993 | Wilson et al. | 364/496 |

FOREIGN PATENT DOCUMENTS 2-301872 12/1990 Japan.
3-245276 10/1991 Japan.

OTHER PUBLICATIONS

CAChe Worksystem, "CAChe Reference Version 3.0", CAChe Scientific A Tektronix Company, 1992, Chapter 1, Appendix C.

Jackson, "Graphical Analysis and Visualization of Three-Dimensional Properties of Molecules and Solids" J. Chem. Inf. Comput. Sci. 1991, v. 31, p. 127–131.

Kao et al., "A Versatile, Efficient, and Interactive Program to Build Molecular Structures for Theoretical Calculations and Chemical Information Systems", vol. 25 Nov. 1985, *Journal of Chemical Information and Sciences* pp. 400–410.

Watt et al. "Chemical Draftsman", *Computers and Chemistry*, vol. 9, No. 4, 1985 pp. 269–277.

A. Koide, "Designing Molecules and Crystals by Computer" IBM Systems Journal, vol. 28, No. 4 pp. 613–627 Dec. 1989.

Naray–Szabo, Gabor et al., "Computational chemistry on APC" International Journal of Quantum Chemistry, vol. 38 (2) pp. 163–171 1990.

Higashi, Tsuneyuki and Kenji Osaki, "A Test for the Computer-Aided Generation of the Cambridge Connectivity Files" Journal of Applied Crystallography vol. 15 pt. 5, pp. 531–536 1 Oct 1982.

*Primary Examiner*—Emanuel T. Voeltz
*Assistant Examiner*—M. Kemper
*Attorney, Agent, or Firm*—Staas & Halsey

[57] ABSTRACT

A molecular design support system comprises a display device, a database for storing information about atoms forming a molecule in terms of atomic component information, and a processing unit for manipulating the atomic component information to assemble a molecular structure in terms of the atomic components. The atomic component information in turn comprises atomic data and bond data, wherein the atomic data comprises: identification data for identifying the atom forming the atomic component; the coordinate of the foregoing atom; the number of the orbitals associated to the atom; and the coordinate showing the position of free end of the orbital included in the atomic component. Bond data comprises: identification data for identifying the atom that is bonded to the free end of the orbital in the atomic component; identification data for identifying the orbital associated with the atom that is bonded to the foregoing free end; and identification data for identifying the bond order of a bond that is established between the atom forming said atomic component and the atom that is attached to the free end.

6 Claims, 11 Drawing Sheets

| Ac-OH | 00000000003D | | |
|---|---|---|---|
| 8 7 | | | |
| 0.0000 | 0.0000 | 0.0000 | C |
| -1.4710 | 0.0000 | -0.0000 | C |
| 0.6100 | 1.0566 | 0.0000 | O |
| 0.6865 | -1.1891 | 0.0000 | O |
| -1.8356 | -0.8909 | -0.5197 | H |
| -1.8356 | -0.0046 | 1.0314 | H |
| -1.8356 | 0.8956 | -0.5117 | H |
| 1.5657 | -1.0070 | -0.0000 | H |

| 1 | 2 | 1 |
| 1 | 3 | 2 |
| 1 | 4 | 1 |
| 2 | 5 | 1 |
| 2 | 6 | 1 |
| 2 | 7 | 1 |
| 4 | 8 | 1 |

ATOMIC NUMBER — ORDER OF BOND

FIG. 3

| MLNM | a1 | a3 | MLD | a4 a5 b1 | b2 b3 | a2 |
|---|---|---|---|---|---|---|
| Acetic-acid | | | | | | |

| ATNO. |
|---|
| 8 |

ATM1 / ACN1

| C | C_sp2 | | C*200020 | | 0 | 0 | 4 |
|---|---|---|---|---|---|---|---|
| 0.000000 | 0.000000 | 0.000000 | 3 | | | | |
| −0.706000 | 0.000000 | 0.000000 | 2 | 1 | 1 | | |
| 0.353000 | 0.611414 | 0.000000 | 3 | 1 | 2 | | |
| 0.353000 | −0.611414 | 0.000000 | 4 | 1 | 1 | | |

ATM2 / ACN2

| C | C_sp3 | | C*300010 | | 0 | 0 | 4 |
|---|---|---|---|---|---|---|---|
| −1.471000 | 0.000000 | −0.000000 | 4 | | | | |
| −0.706000 | −0.000000 | −0.000000 | 1 | 1 | 1 | | |
| −1.725985 | −0.623004 | −0.363419 | 5 | 1 | 1 | | |
| −1.725985 | −0.003228 | 0.721247 | 6 | 1 | 1 | | |
| −1.725985 | 0.626232 | −0.357828 | 7 | 1 | 1 | | |

ATM3 / ACN3

| O | O_carbonyl | | O*200012 | | 0 | 0 | 2 |
|---|---|---|---|---|---|---|---|
| 0.810000 | 1.056551 | 0.000000 | 1 | | | | |
| 0.353000 | 0.611414 | 0.000000 | 1 | 2 | 2 | | |

ATM4 / ACN4

| O | O_ether | | O*300022 | | 0 | 0 | 2 |
|---|---|---|---|---|---|---|---|
| 0.686500 | −1.189053 | 0.000000 | 2 | | | | |
| 0.353000 | 0.611414 | 0.000000 | 1 | 3 | 1 | | |
| 1.342267 | −1.067158 | −0.000000 | 8 | 1 | 1 | | |

ATM5 / ACN5

| H | * | | H*300010 | | 0 | 0 | 1 |
|---|---|---|---|---|---|---|---|
| −1.835645 | −0.890937 | −0.519713 | 1 | | | | |
| −1.725985 | −0.623004 | 0.363419 | 2 | 2 | 1 | | |

ATM6 / ACN6

| H | * | | H*300010 | | 0 | 0 | 1 |
|---|---|---|---|---|---|---|---|
| −1.835645 | −0.004818 | 1.031431 | 1 | | | | |
| −1.725985 | −0.003228 | 0.721247 | 2 | 3 | 1 | | |

ATM7 / ACN7

| H | * | | H*300010 | | 0 | 0 | 1 |
|---|---|---|---|---|---|---|---|
| −1.835645 | 0.895553 | −0.511717 | 1 | | | | |
| −1.725986 | 0.626232 | −0.357828 | 2 | 4 | 1 | | |

ATM8 / ACN8

| H | * | | H*300051 | | 0 | 0 | 1 |
|---|---|---|---|---|---|---|---|
| −1.865727 | −1.007033 | −0.000000 | 1 | | | | |
| 1.342267 | −1.067158 | −0.000000 | 4 | 2 | 1 | | |

CH3COOH

Carbon-SP2    Oxygen-Carbonyl    Hydrogen    Hydrogen

FIG. 9 (A)

| | | | | | | |
|---|---|---|---|---|---|---|
| 1 | | | | | | |
| C | C_sp2 | | C*200020 | 0 | 0 | 4 |
| | -0.023300 | 0.087600 | 0.000000 | 3 | 0 | |
| | -0.636122 | -0.262876 | 0.000000 | 0 | 0 | 0 |
| | -0.020407 | 0.793600 | 0.000000 | 0 | 0 | 0 |
| | 0.586657 | -0.267856 | 0.000000 | 0 | 0 | 0 |

- Rows 2–3: ATM1
- Rows 4–6: ACN1

FIG. 9 (B)

| | | | | | | |
|---|---|---|---|---|---|---|
| 2 | | | | | | |
| C | C_sp2 | | C*200020 | 0 | 0 | 4 |
| | -0.023300 | 0.087600 | 0.000000 | 3 | 0 | |
| | -0.636122 | -0.262876 | 0.000000 | 0 | 0 | 0 |
| | -0.020407 | 0.793600 | 0.000000 | 2 | 1 | 2 |
| | 0.586657 | -0.267856 | 0.000000 | 0 | 0 | 0 |
| O | O_carbonyl | | O*200012 | 0 | 0 | 2 |
| | -0.018300 | 1.307600 | 0.000000 | 1 | 0 | |
| | -0.020407 | 0.793600 | 0.000000 | 1 | 2 | 2 |

- ATM1 / ACN1 / ATM2 / ACN2

FIG. 9 (C)

| | | | | | | |
|---|---|---|---|---|---|---|
| 4 | | | | | | |
| C | C_sp2 | | C*200020 | 0 | 0 | 1 |
| | -0.023300 | 0.087600 | 0.000000 | 3 | 0 | |
| | -0.636122 | -0.262876 | 0.000000 | 4 | 1 | 1 |
| | -0.020407 | 0.793600 | 0.000000 | 2 | 1 | 2 |
| | 0.586657 | -0.267856 | 0.000000 | 3 | 1 | 1 |
| O | O_carbonyl | | O*200012 | 0 | 0 | 2 |
| | -0.018300 | 1.307600 | 0.000000 | 1 | 0 | |
| | -0.020407 | 0.793600 | 0.000000 | 1 | 2 | 2 |
| H | * | | H*300010 | 0 | 0 | 1 |
| | 0.870900 | -0.433500 | 0.000000 | 1 | 0 | |
| | 0.586657 | -0.267856 | 0.000000 | 1 | 3 | 1 |
| H | * | | H*300010 | 0 | 0 | 1 |
| | -0.921700 | -0.426200 | 0.000000 | 1 | 0 | |
| | -0.636122 | -0.262878 | 0.000000 | 1 | 1 | 1 |

- ATM1 / ACN1 / ATM2 / ACN2 / ATM3 / ACN3 / ATM4 / ACN4

MOLECULAR DESIGN SUPPORT SYSTEM

This application is a continuation of application Ser. No. 07/993,775, filed Dec. 21, 1992, now abandoned.

BACKGROUND OF THE INVENTION

MOLECULAR DESIGN SUPPORT SYSTEM

The present invention generally relates to molecular design support systems for creating or modifying the structure of molecules in a computer by using graphic display function of the computer, and more particularly to a molecular design support system for creating a new molecular structure or modifying an existing molecular structure in a computer by representing the molecular structure in terms of structural components that form the molecular structure.

With the increased computational power of workstations and personal computers, various calculations in the field of theoretical chemistry such as molecular orbital theory, molecular mechanics, molecular dynamics, and the like, are becoming the matter of practical and routine investigation process. In the field of chemistry, material sciences, and pharmaceuticals in particular, such theoretical calculation provides a powerful tool for designing a new molecule. When conducting such a calculation, it is necessary to provide three-dimensional structural data of the molecules or compounds that are subjected to the investigation, to the computer as input data. It is generally known that the reliability of the calculation heavily depends on the quality of the input data supplied to the computer.

In the conventional molecular design support systems, the structural information of molecules are represented in terms of: (a) first data group that represents data about individual atoms forming the molecule such as the type of the atoms (elements) that constitute the molecule, the coordinate and valence of the atoms, and the like; and (b) second data group that represents data about the chemical bond in the molecule such as the identification of the atoms that are connected by the bond, the order of the bond, and the like.

FIGS. 1(A) and 1(B) show an example of the structural information that has been used conventionally, wherein FIG. 1(A) represents the structural formula of acetic acid having the formula $CH_3COOH$ while FIG. 1(B) shows the structural information of the acetic acid shown in FIG. 1(A). The structural information of FIG. 1(B) is represented in terms of the "mol-file" format proposed by MDL Corporation.

Referring to FIG. 1(B), it will be noted that the first field 1 represents the name and code number of the acetic acid molecule, the second field 2 represents the number of atoms (=8) included in the molecule and the number of bonds (=7) included in the molecule, and the third field 3 represents the atomic data that includes three-dimensional coordinate of the atoms included in the molecule and the type of the atoms or elements forming the molecule. Further, the fourth field 4 identifies each of the atomic pairs forming the chemical bonds in terms of the identification code for identifying the atomic type of the atoms forming the atomic pair and the order of the chemical bond formed therebetween.

The data represented in FIG. 1(B), however, is not convenient for a user to construct a new molecular structure. It should be noted that the procedure for constructing a new molecule includes the steps for specifying the mutual relationship between various structural elements forming the molecular structure. For example, one has to specify the bond length, bond angle, and the torsional angle between various functional groups or constructing a new molecular structure. Obviously, the data shown in FIG. 1(B) is not convenient for such a purpose. On the other hand, such a manual procedure requires expertise of the operator and tends to invite human errors. In addition to the foregoing problems, the process shown in FIG. 1(B) raises another problem in that a very complex processing is necessary when modifying an existing molecular structure such as repeatedly referring to the data in the field 3 and field 4. Thereby, the response of the processing becomes slow and the operation of the system becomes inevitably difficult.

In order to overcome the foregoing problems, it is proposed to prepare in advance the structural data for each of the stable structural components such as fundamental compounds and functional groups and to combine the structural components to form a new molecular structure. By using the sophisticated graphic user interface (GUI) in combination with the foregoing process, one can easily obtain structural data of new molecules. On the other hand, such a process has a drawback in that it requires a preparation of extensive database for the structural components such as the fundamental compounds and functional groups. In addition, it is necessary to determine the bond length, upon substitution of the structural components, with respect to the atomic pair that is formed as a result of the substitution of the structural components. Thereby, the database has to be referred to frequently upon processing, and the time that is needed for the processing becomes inevitably longer.

Alternatively, there is a proposal to bond an atom or an atomic group to an unfilled valence bond of atoms that form a part of the molecule, based upon an empirical law, such that the atom or atomic group is attached automatically by the computer system to an optimum location of the molecule. Although the latter process is simpler to implement for the operator, there is a possibility that the obtained structure may be totally different from the intended structure. This problem tends to occur when arbitrary factors exist in the determination of the structure as in the case where there exists a freely rotatable single-bond associated with low energy barrier or as in the case where there are a plurality of conformations in a ring structure.

SUMMARY OF THE INVENTION

Accordingly, it is a general object of the present invention to provide a novel and useful molecular design support system wherein the foregoing problems are eliminated.

Another and more specific object of the present invention is to provide a molecular design support system that is easy to operate and can be used efficiently for creating or modifying a molecular structure.

Another object of the present invention is to provide a molecular design support system capable of forming a molecular structure with an improved precision.

Another object of the present invention is to provide a molecular design support system for creating and/or modifying a molecular structure, comprising:

display means supplied with molecular data representing a molecular structure for displaying said molecular structure graphically;

database means for storing information about atoms forming a molecule in terms of atomic component information, said atomic component information representing information about atomic components that are assembled to form a molecular structure of said molecule, each of said atomic components including an atom and at least one orbital associated therewith, said atomic component information comprising, for each of said atomic components, atomic data and bond data, said atomic data comprising: first identification data for identifying the atomic type of said atom that forms said atomic component, first coordinate data representing the position of said atom that forms said atomic component; number data representing the number of the orbitals associated to said atom forming said atomic component; and second coordinate data showing the position of a free end of the orbital for each of said orbitals in said atomic component; said bond data comprising: second identification data for identifying the atomic type of an atom that is bonded to the free end of said hybrid orbital in said atomic component; third identification data for identifying the orbital associated with said atom that is bonded to said free end of said atom that forms said atomic component; and fourth identification data for identifying the bond order of a bond that is established between said atom forming said atomic component and said atom that is attached to said free end; and processing means for manipulating said atomic component information to assemble a molecular structure in terms of said atomic components, said processing means producing said molecular data in correspondence to said assembled molecular structure.

According to the present invention, one can eliminate the time-consuming processes such as repeatedly referring to the tables containing chemical bond information as well as various decisions that has to be made by the operator based upon the knowledge of chemistry, when constructing a molecular structure. Thereby, the process for constructing or modifying the molecular structure is significantly simplified and the efficiency of operation is significantly improved. It should be noted that the structural component used in the present invention contains not only the information about the coordinate of the atom that forms the structural component but also the information about the hybrid orbital(s) that accompany the atom. More specifically, the structural component is given as an entity that includes the information about the bond angle in addition to the type and coordinate of the atom that forms the structural component, and there is no need to specify the bond angle individually when assembling a molecular structure. Further, one can obtain the bond length simply as a sum of the hybrid orbitals that are connected with each other. As the operation for assembling the molecular structure is displayed graphically on the display device, the operator can achieve the necessary operation very easily, without calculating the position of the individual hybrid orbitals. Further, the molecular design support system of the present invention is also effective in the construction of the stereoisomers.

Other objects and further features of the present invention will become apparent from the following detailed description when read in conjunction with the attached drawings.

BRIEF DESCRIPTION OF THE DRAWINGS

FIG. 3 is a diagram showing the representation of molecular structure in a database that is used in the system of FIG. 2

FIGS. 9(A)–9(C) are diagrams showing the progressive change of the molecular structure data associated with the process of FIGS. 7(A)–7(C).

DETAILED DESCRIPTION OF THE PREFERRED EMBODIMENTS

Figures 1A, 1B:
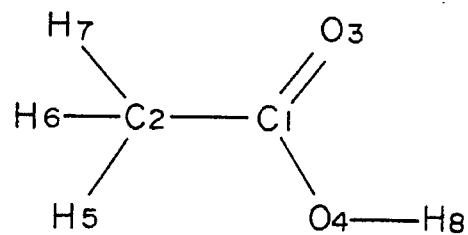
FIGS. 1(A) and 1(B) are diagrams respectively showing the structural formula of an acetic acid molecule and a conventional representation of the molecular structure of acetic acid.
Figure 2:
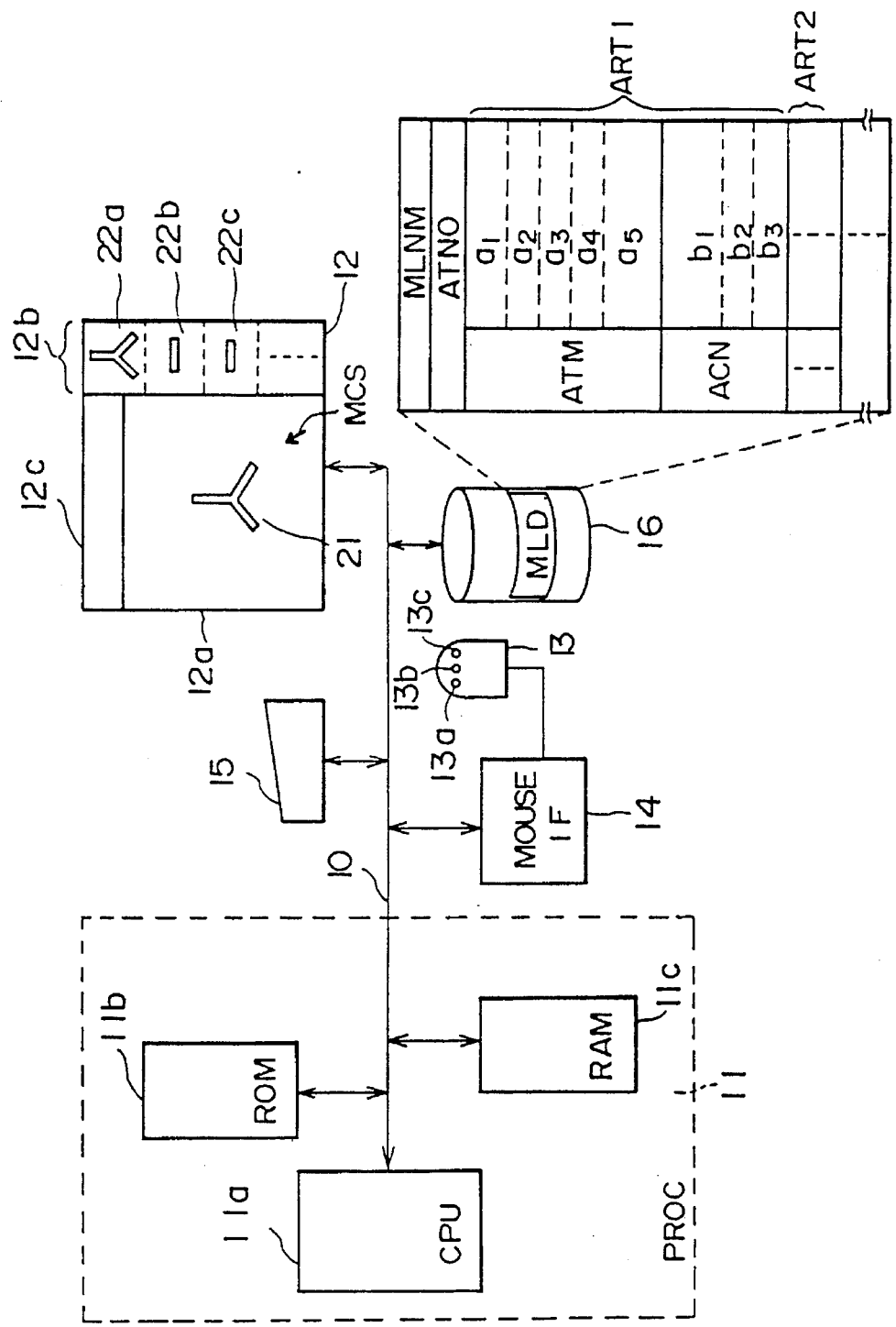
FIG. 2 is a block diagram showing the molecular design support system according to a first embodiment of the present invention.

FIG. 2 shows the overall construction of the molecular design support system according to an embodiment of the present invention.

Referring to FIG. 2, the system has a typical construction of a personal computer and includes a system bus 10 to which a processing unit 11 is connected. As usual, the processing unit 11 includes a CPU 11a connected to the bus 10, and a random access memory 11c connected to the bus 10 cooperates with the CPU 11a. Further, a read-only memory 11b also connected to the bus 10 supplies various system information to the CPU 11a via the bus 10 as usual.

The system bus 10 extends throughout the system and a display unit 12 is connected thereto via a video interface not illustrated in FIG. 2. Further, a pointing device 13 such as a mouse is connected to the bus 10 via an interface unit 14, in addition to the usual keyboard represented by a numeral 15. Thereby, a graphic user interface (GUI) for controlling the operation of the system by the graphic information displayed in the monitor screen of the display unit 12 is formed. Further, an external storage device 16, typically of a hard disk device, is connected to the system bus 10 via a suitable interface not illustrated, and the storage device 16 stores therein various software including the graphic user interface program and the control program of the molecular design support system.

In the molecular design support system of the present invention, it should be noted that the control program sets a database in the hard disk device 16 for storing various component data for constructing a molecular structure as will be described in detail below. Further, the database stores the created molecular structure.

In the present invention, the molecular structure is represented in terms of various atomic components each formed essentially of an atom and one or more electron orbitals that accompany the atom forming the atomic component. Thereby, the molecular structure is formed by assembling various atomic components together and jointing the orbitals of different atomic components to form a chemical bond. As the atom and orbital(s) are given in the form of unitary atomic component in the present invention, the operator can handle the atomic component as a unitary component or building block in the monitor screen of the display device 12, and the operator can construct a molecular structure easily by using the GUI function of the computer. In FIG. 2, it should be noted that the monitor screen of the display device 12 is divided into a main window 12a for representing the molecular structure of the molecule under investigation such as a molecule 21, a first sub-window 12b for representing a number of available atomic components 22a, 22b, 22c, . . . , and a second sub-window for representing various menus of the program.

In the foregoing treatment, it should be noted that the angle formed between various hybrid orbitals of an atom is set to a predetermined angle depending on the type of the hybrid orbital. For example, the sp3 orbitals of a carbon atom form the bond angle of 109.5 degrees. Such a carbon atom having the sp3 state appears in the saturated chain hydrocarbons and is characterized by the tetrahedral coordination. Thereby, it becomes possible to handle the atom as well as the hybrid orbitals associated with the atom as a rigid, unitary body having a form, not a mere point in the three-dimensional space. Hereinafter, the representation of the molecular structure in the database formed in the hard disk 16 according to the principle above, will be described in detail.

Referring to FIG. 2, it will be noted that the database includes: (a) identification data MLNM for identifying the molecule under investigation; (b) atom number data ATNO for representing the number of atoms included in the molecule; (c) atomic data ATM for representing various information of the atom as well as electron orbital(s) associated with the atom for each of the atoms forming the molecule as will be described later; and (d) bond data ACN for identifying the atom as well as the associated orbital that establishes a chemical bond with the atom that is designated by the atomic data ATM. In correspondence to a number of atoms included in the molecule, there may exist a number of atomic data ATM and corresponding bond data ACN. Thereby, the data MLNM, ATNO, ATM and ACN form molecular structural information MLD.

In the molecular structural information MLD of FIG. 2, each atomic data ATM includes information about the hybrid orbitals in addition to information about the type and coordinate of the atom, and thus, the atom and the corresponding hybrid orbital(s) are treated as a unitary data set corresponding to the foregoing atomic component of the molecule. Hereinafter, the content of the data ATM will be examined in detail.

FIG. 3 shows an example of the molecular structural information MLD of an acetic acid molecule that includes eight atoms in all, i.e., a single carbon atom C(1) having the sp3 state and forming the methyl group, a single carbon atom C(2) having the sp2 state and forming the carboxyl group, a single oxygen atom O(3) having the sp2 state and forming the carbonyl group, a single oxygen atom O(4) having the sp3 state and forming the ether group, and four hydrogen atoms H(5)–H(8). See the structural formula represented in FIG. 4 in the half vector form.

Referring to FIG. 3, it will be noted that the information MLD includes, in addition to the data MNLM and ATNO, atomic data ATM1–ATM8 as well as corresponding bond data ACN1–ACN8 in correspondence to each of the eight atoms forming the acetic acid molecule, wherein each atomic data and the corresponding bond data form component information ART1, ART2, . . . in correspondence to the atomic component described previously. See FIG. 2. For example, the atomic data ATM1 and the bond data ACN1 form the component data ART1.

It should be noted that each of the atomic data ATM1–ATM8 includes: a first field $a_1$ for identifying the atom forming the atomic component; a second field $a_2$ for identifying the valence state of the atom; a third field $a_3$ for identifying the coordinate of the atom; a fourth field $a_4$ for identifying the number of the hybrid orbitals formed in the atom; and a fifth field $a_5$ for representing the coordinate of the free end of each hybrid orbital that is formed at the atom forming the atomic component. For example, the data ATM1 shown in FIG. 3 includes the data C—sp2 in the first field $a_1$ indicative of the carbon atom having the sp2 hybrid orbital. The second field $a_2$, in turn, includes the number "4" indicating the valence number of the carbon atom designated in the first field $a_1$. Further, the third field $a_3$ is used to represent the three-dimensional coordinate of the foregoing carbon atom designated in the field $a_1$. In the present case, the carbon atom is located at the origin and the X-, Y- and Z-coordinate are all zero as represented by (0.000000, 0.000000, 0.000000). The value "3" in the fourth field $a_4$ of the data ATM1 in turn indicates the fact that the sp2 state of carbon includes three hybrid orbitals, and the numerals in the fifth field $a_5$ represent respectively the three-dimensional coordinates of the free end of the three hybrid orbitals identified in the fourth field $a_4$. In the illustrated example, the three hybrid orbitals have respective free ends at (−0.706000, 0.000000, 0.000000), (0.353000, 0.611414, 0.000000) and (0.353000, −0.611414, 0.000000).

Next, the data ACN1–ACN8 will be explained with reference to FIG. 3, wherein only the data ACN1 will be examined for the sake of simplicity of the explanation.

Figure 4:
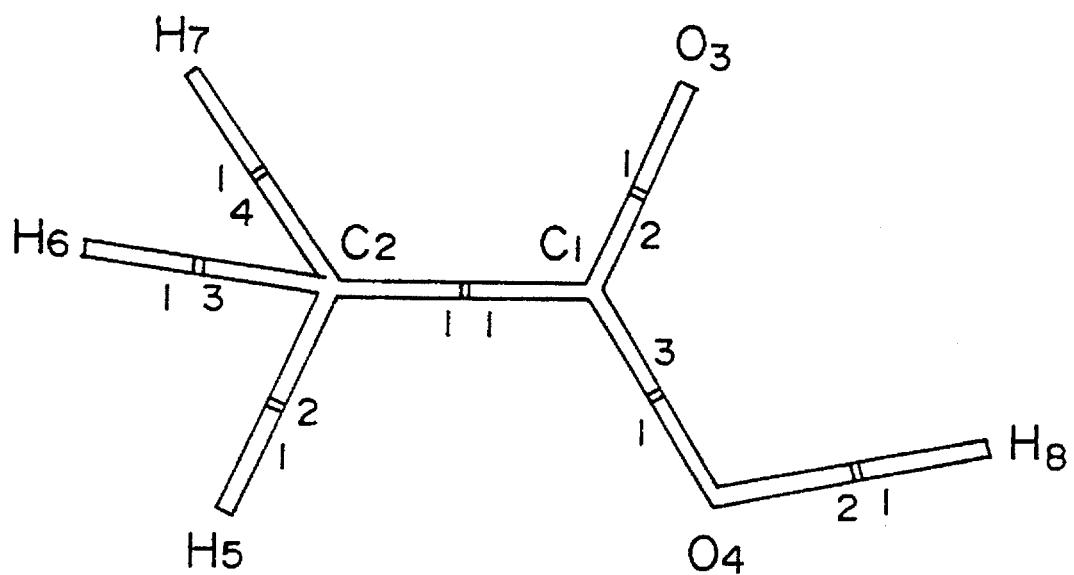
FIG. 4 is a diagram showing the structure of acetic acid that is created in the molecular design support system of FIG. 2.

Referring to FIGS. 2 and 3, it will be noted that the data ACN includes the data fields $b_1$, $b_2$ and $b_3$, wherein the field $b_1$ is used for storing the data that identifies the atom that is bonded to the orbital free end designated in the field $a_5$, while the field $b_2$ is used for storing the data that identifies the orbital associated with the atom that is designated in the field $b_1$. Further, the field $b_3$ is used for storing the identification of the order of the orbital designated in the field $b_2$. Thus, the data ACN1 of FIG. 3 indicates that the carbon atom C(2) shown in FIG. 4 and being designated by the numeral "2" as represented in the field $b_1$, is bonded to the free end of the sp2 orbital locating at the coordinate (−0.706000, 0.000000, 0.000000) by connecting the orbital 1 as represented in the field $b_2$, to form a single bond as represented in the field $b_3$. Similarly, the oxygen atom O(3) designated in the field $b_1$ is bonded to the free end of the hybrid orbital at (0.353000, 0.611414, 0.000000) by bonding the orbital 1 as indicated in the field $b_2$, to form a double bond as indicated in the field $b_3$. Further, the oxygen atom O(4) establishes a bond to the free end of the orbital at the coordinate (0.353000, −0.611414, 0.000000) as indicated in the field $b_1$ by bonding the orbital 1 of the O(4) atom to the foregoing free end as indicated by the field $b_2$, to form a single bond as indicated in the field $b_3$. Similarly, the atomic data ATM2–ATM8 as well as the bond data ACN2–ACN8 are represented as indicated in FIG. 3, and the structure of the acetic acid is obtained in the half vector form as indicated in FIG. 4. In other words, the half-vector representation of FIG. 4 corresponds to the representation shown in FIG. 3.

Figure 5A:
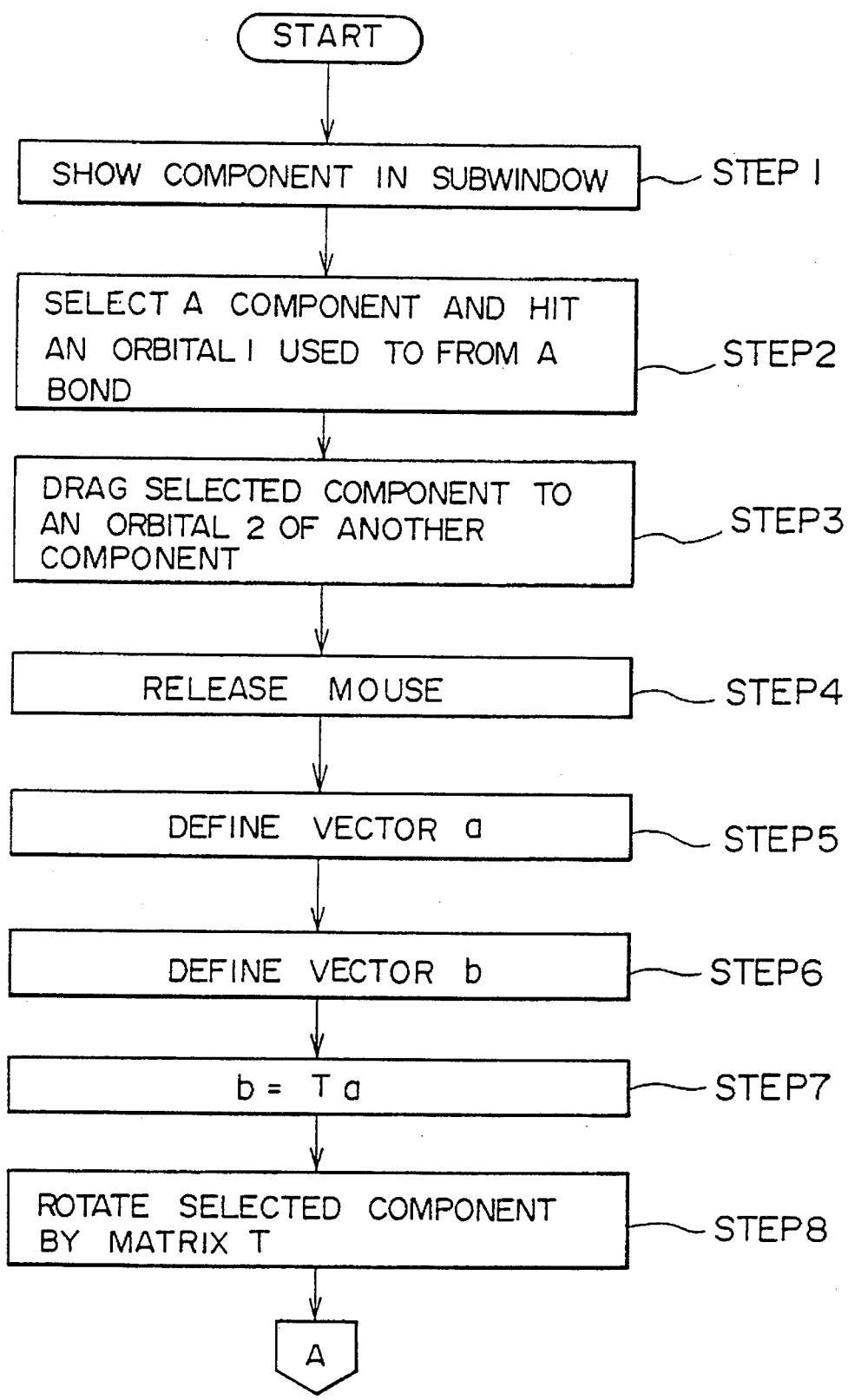
FIGS. 5(A)–5(C) are flowcharts showing the process for creating a molecular structure from the structural components stored in the database by the molecular design support system of FIG. 2.
Figure 5B:
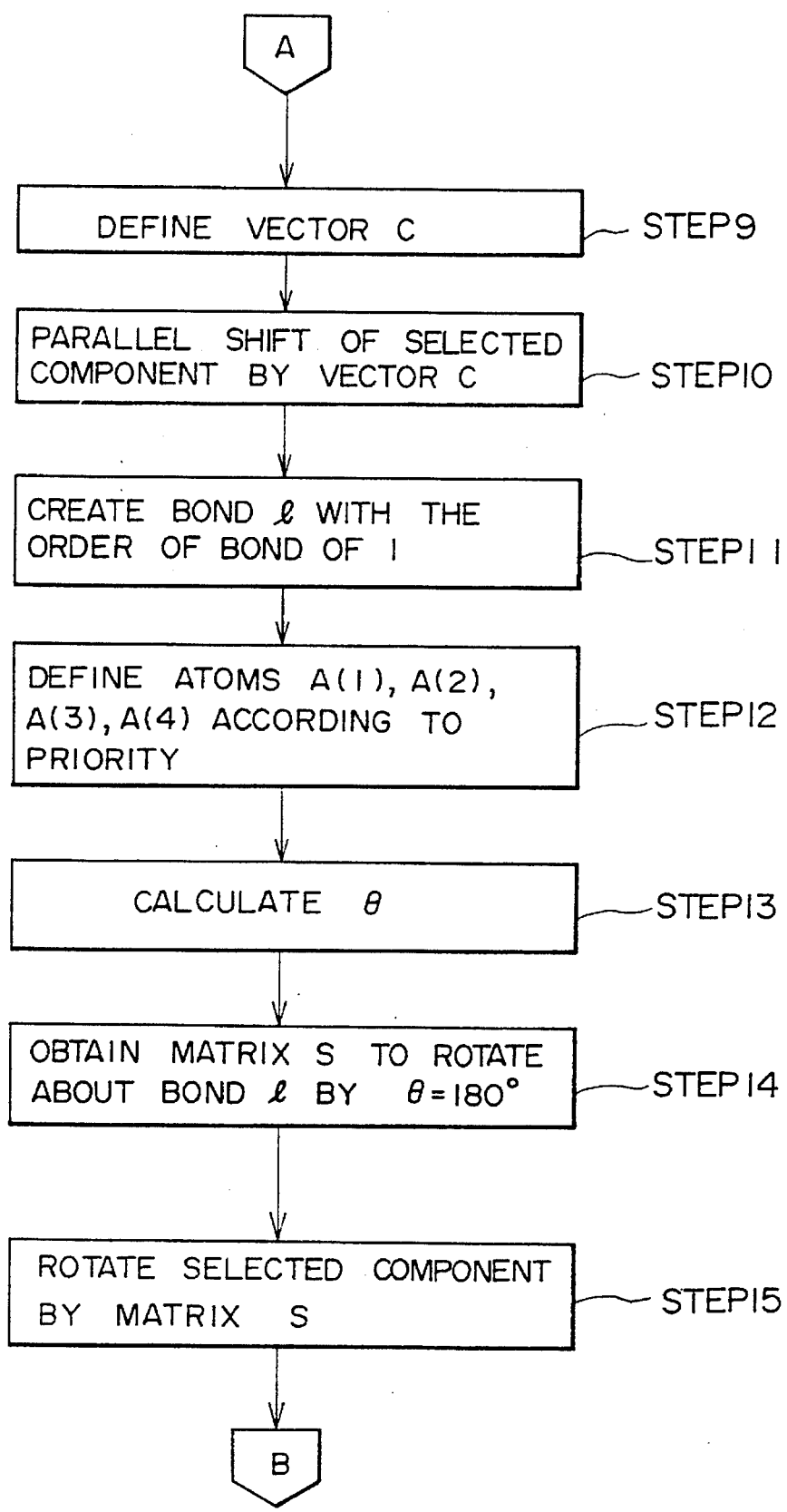
Figure 5C:
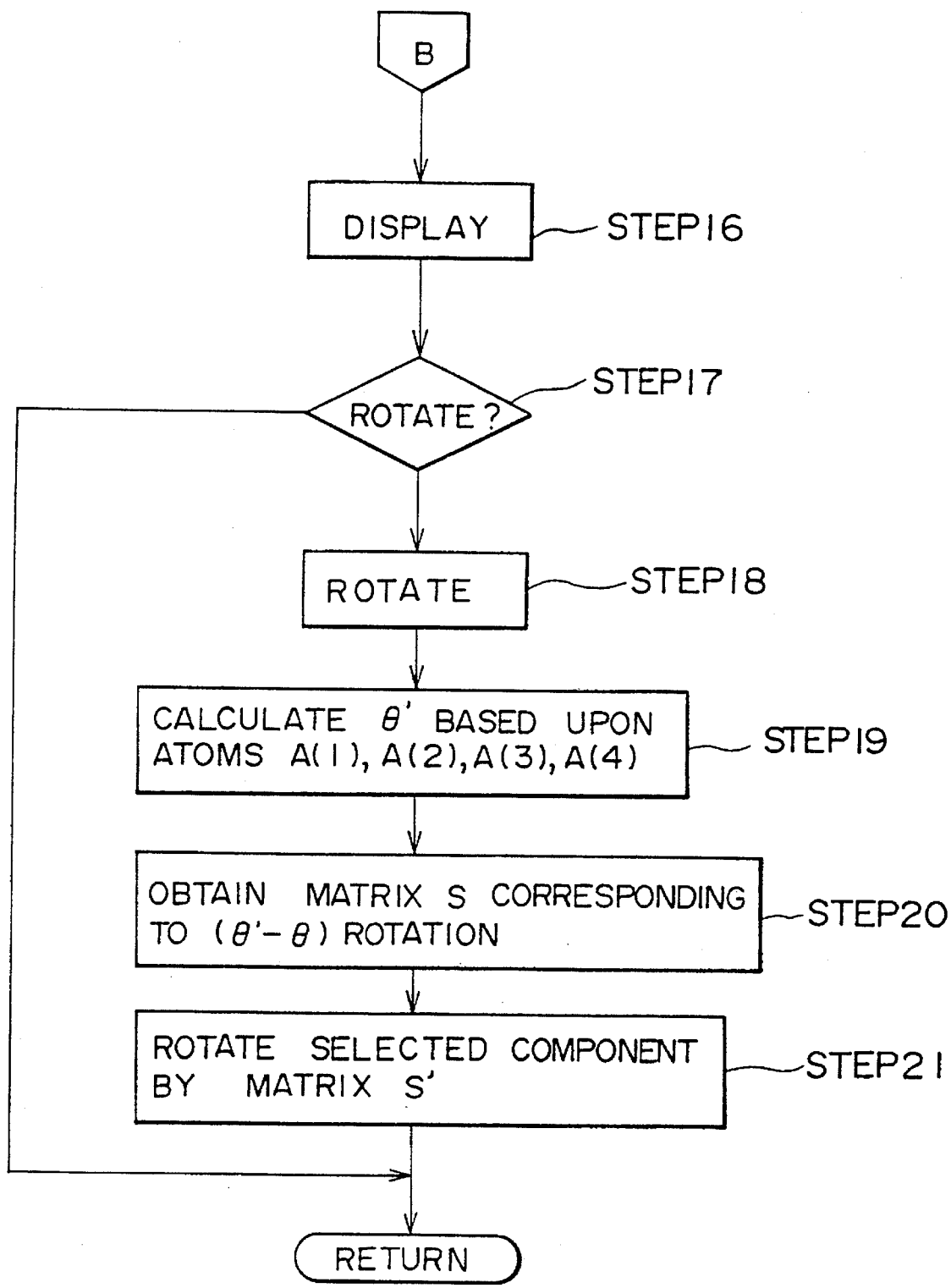

In the molecular design support system of FIG. 2, the molecular structural information MLD is formed by assembling the atomic components shown in FIG. 4 and including the atoms such as C(1), C(2), O(3), O(4), H(5)–H(8), by using the graphic user interface function of the computer system. Hereinafter, the process for constructing the molecular structure by using the molecular design support system of FIG. 2 will be explained with reference to FIGS. 5(A)–5(C).

Referring to the drawings, the process starts with a step 1 wherein the atomic components 22a, 22b, 22c, . . . are represented in the sub-window 12b. Next, in a step 2, one of the atomic components such as the atomic component 21 is selected by hitting the same by a mouse, and the selected atomic component is dragged to the main window 12a in a subsequent step 3. Next, in a step 4, the mouse is released, and the dragging of the selected atomic component is completed.

When there exists a atomic component already in the main window 12a, the step 2 is conducted to select a new atomic component that is to be connected to the preexisting atomic component. Thereby, the step 2 is conducted such that an orbital, designated as Orb1 and is used for establishing a chemical bond with the existing component, is hit by the mouse, upon selection of the newly selected atomic component. Thereby, the newly selected atomic component is dragged in the step 3 to an orbital Orb2 of the preexisting atomic component, wherein the orbital Orb2 represents the orbital to which the orbital Orb1 is to be connected.

In this case, the step 4 for releasing the mouse activates a series of steps wherein the selected component is rotated aligned for bonding to the preexisting atomic component. Thus, in a step 5, a vector a is defined as the vector that extends from the free end (located at P1) of the orbital Orb1 to the atom to which the orbital Orb1 belongs. In other words, the vector a extends from the coordinate represented in the field $a_5$ to the coordinate represented in the field $a_3$ of FIG. 3.

Next, in a step 6, another vector b is defined as a vector extending from the atom in the preexisting atomic component (located at $P_2$) to the free end of the orbital Orb2 that extends from the foregoing atom at $P_2$. Further, in a step 7, a transformation matrix T is obtained as a matrix that rotates the vector a to form the vector b. Thereby, there holds a relationship b=Ta. Further, in a step 8 that follows the step 7, the newly attached atomic component is rotated with respect to the entirety thereof by the matrix T.

Next, in a step 9, a vector c is defined as a vector that extends from the coordinate $P_1$ to the coordinate $P_2$, and the newly selected atomic component is translated by the vector c in a subsequent step 10. Further, in a step 11, a bond 1 is created with the order defined in the field $b_3$ by connecting the orbitals Orb1 and Orb2.

Figure 6:
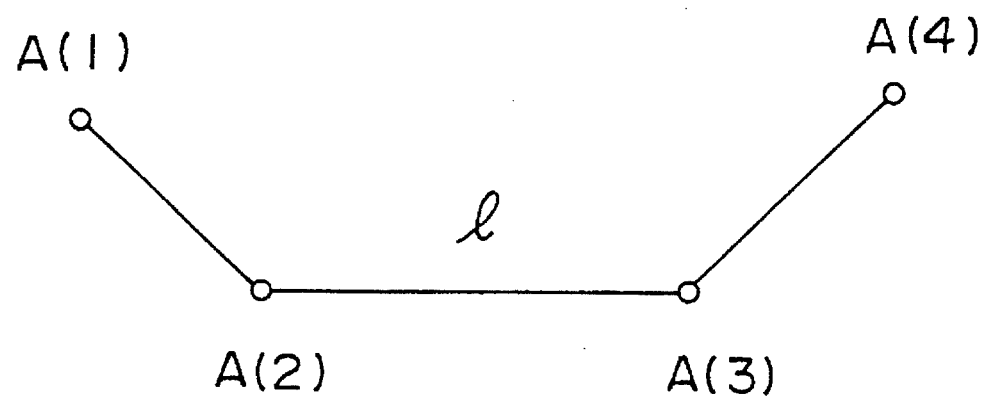
FIG. 6 is a diagram for explaining the adjustment of the torsional angle.

Next, the atoms thus bonded together are given with a predetermined priority order in a step 12 according to the standard procedure that is used commonly in the stereochemistry for determining the configuration of molecules. Further, the atoms that are connected to the bond 1 and having the highest priority are selected as shown in FIG. 6. In FIG. 6, the atoms A(2) and A(3) form the bond 1 while the atom (1) is the atom connected to the atom (2) and having the highest priority. Similarly, the atom (4) is the atom connected to the atom (3) and having the highest priority.

After the step 12, a torsional angle θ is calculated in a step 13 as the angle formed between the plane that includes the atoms A(1), A(2) and A(3) and the plane that includes the atoms A(2), A(3) and A(4). Further, in a step 14, a transform matrix S that represents the relative rotation of the atom A(1) with respect to the atom A(4) about the bond 1, is determined such that the torsional angle θ becomes 180 degrees (θ=180°). Further, in a subsequent step 15, the newly selected atomic component is rotated about the bond 1 by using the transform matrix S thus determined. Further, the structure thus obtained is displayed in the monitor screen 12a of the display device 12 by supplying the molecular structural data corresponding to the structure thus obtained. Further, by repeating the steps 1–15, one can construct any complex molecular structure as desired.

Now, when the user wishes to modify a preexisting structure by rotating a first atomic component with respect to a second atomic component that is connected to the first atomic component by the bond x, a command is given in a step 17 that activates a series of rotation steps. Thus, in a step 18, the atomic configuration A(4)–A(3)–A(2) is rotated about the bond 1 with respect to the atomic configuration A(1)–A(2)–A(3) by a desired angle θ' by using the mouse 13. Next, the rotational angle θ' thus specified is detected in a step 19, and a corresponding transform matrix S' is calculated in a step 20 such that the matrix S' represents a rotation about the bond 1 by an angle of θ–θ'. Further, both atomic components are rotated with each other in a step 21 by the angle θ–θ' by using the transform matrix S' thus obtained. Thereby, one can modify the existing structure within the degree of freedom provided by the nature of chemical bond.

Figure 7A:
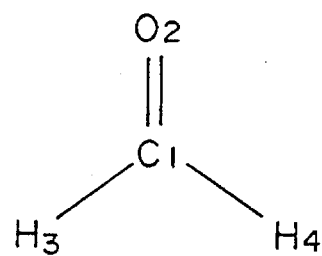
FIGS. 7(A)–7(C) are diagrams showing the process for creating a molecular structure graphically.
Figure 7B:
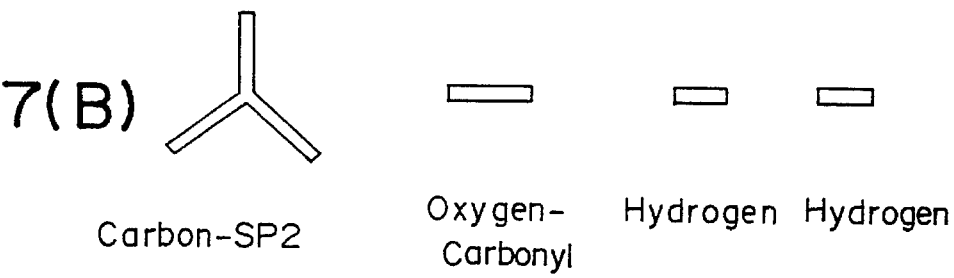
Figure 7C:
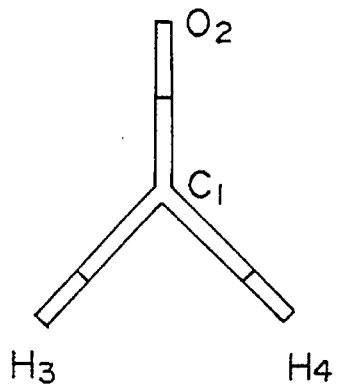
Figure 8A:
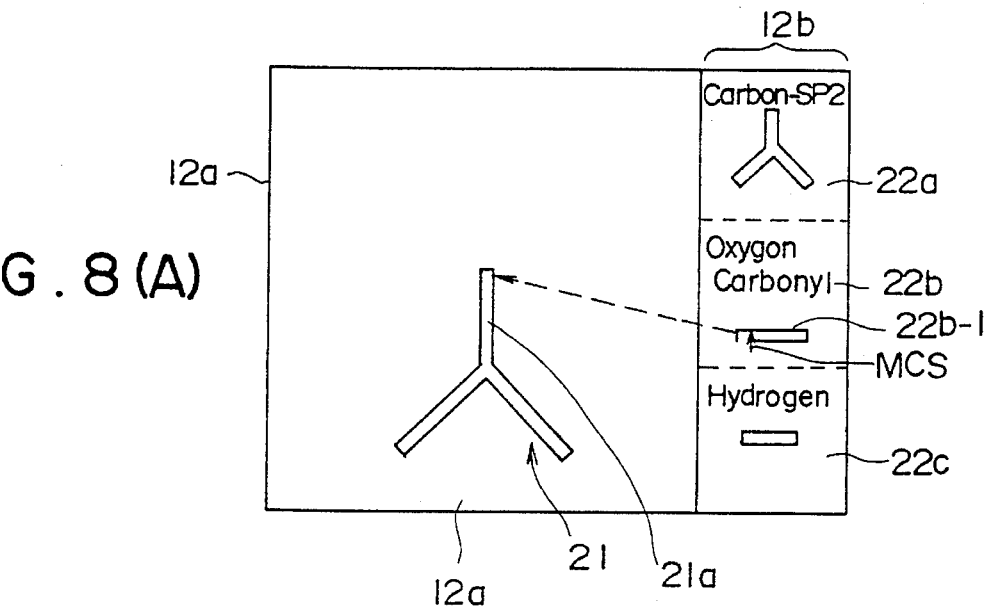
FIGS. 8(A) and 8(B) are diagrams showing the process for creating a molecular structure corresponding to FIGS. 7(A)–7(C) as represented in the monitor device of the system of FIG. 2.
Figure 8B:
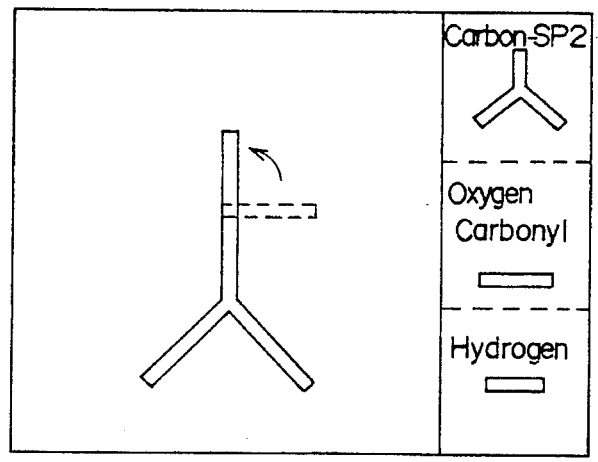

FIGS. 7(A)–7(C) show the foregoing processes for constructing a new molecule graphically for the case of a formaldehyde molecule, while FIGS. 8(A) and 8(B) show how the process proceeds in the monitor screen of the display device 12. When constructing a formaldehyde molecule shown in FIG. 7(A), one needs a C—sp2 component, an oxygen-carbonyl component and two hydrogen components shown in FIG. 7(B), wherein the oxygen-carbonyl component is attached to the double bond of the C—sp2 component while the hydrogen components are attached to the single bonds of the C—sp2 component as shown in FIG. 7(C).

The actual process proceeds as follows.

First, the operator selects the C—sp2 component 22a from the sub-window 12b and drags the same to an arbitrary location of the main window 12a. Next, the operator selects the oxygen-carbonyl component 22b from the sub-window 12b by hitting the hybrid orbital $22_{b-1}$ of the component 22b by the mouse 13 and drags the same to the free end of the orbital 21a of the molecule 21 to which the oxygen carbonyl component 22b is to be attached. Thereby, the oxygen-carbonyl component 22b is attached to the orbital 21a at first as indicated by a dotted line in FIG. 8(B). This state corresponds to the step 4. Next, the oxygen-carbonyl component 22b is rotated and translated in alignment with the orbital 21a as indicated by a continuous line in FIG. 8(B) as a result of the rotation by the transform matrix T and the translational vector C, and the orbital $22_{b-1}$ and the orbital 21a establishes a chemical bond in this state.

FIGS. 9(A)–9(C) show the transition of the content of the molecular structural information for the formaldehyde molecule with the progress of the foregoing assembling process of the components. There, FIG. 9(A) represents only the C—sp2 component as represented by the single data ATM1 and corresponds to the state of FIG. 8(A). It should be noted that the data ACN1 is blank, reflecting the situation that the C—sp2 component is free and no atom is bonded thereto.

FIG. 9(B), on the other hand, shows the state corresponding to FIG. 8(B) wherein the oxygen carbonyl component 22b is bonded to the C—sp2 component. There, it will be noted that the state of FIG. 9(B) includes the data ATM1 for the C—sp2 component and the data ATM2 for the oxygen-carbonyl component, and the data ACN1 and the data ACN2 represent the mutual bonding of the C—sp2 component and the oxygen-carbonyl component. Further, FIG. 9(C) represents the state corresponding to FIG. 7(C) wherein the hydrogen components are attached further to the structure of FIG. 9(B).

According to the present invention, one can eliminate the time-consuming processes such as repeatedly referring to the tables containing chemical bond information as well as various decisions that has to be made by the operator based upon he knowledge of chemistry, when constructing a molecular structure. Thereby, the process for constructing or modifying the molecular structure is significantly simplified and the efficiency of operation is significantly improved. As discussed already, it should be noted that the atomic component used in the present invention contains not only the information about the coordinate of the atom that forms the atomic component but also the information about the hybrid orbital(s) that accompany the atom. More specifically, the atomic component is given as an entity that includes the information about the bond angle in addition to the type and coordinate of the atom that forms the atomic component, and there is no need to specify the bond angle individually when assembling a molecular structure. Further, one can obtain the bond length simply as a sum of the hybrid orbitals that are connected with each other. As the operation for assembling the molecular structure is displayed graphically on the display device, the operator can achieve the necessary operation very easily, without calculating the position of the individual hybrid orbitals. Further, the molecular design support system of the present invention is also effective in the construction of the stereoisomers.

In the atomic component data shown in FIG. 3, it should be noted that the information about the valence state is included in the field $a_2$. Thereby, it is possible to calculate the order of the hybrid bond connecting two atomic components, based upon the valence state and the order of the hybrid orbital(s) of the atoms that are included in the respective atomic components. More specifically, the order of hybrid orbital is determined generally from the fact that the number of valence of an atom is equal to the sum of the order of the bonds that are formed at that atom, provided that the valence of the atom is filled. In the case when the atom has electric charges, the electric charge is added to the foregoing sum of the order of the bonds.

For example, in the case where the number of valence and the number of hybrid orbitals are equal to each other in an atom, the order of the hybrid bond of the atom is restricted to one. Thereby, the atomic component that includes the atom can take only the single bond state. Further, the order of the bond is equal to the number of the valence of the atom when the atom has only one hybrid orbital.

In other cases, the order of bond is not determined uniquely. Even in such cases, the possibility of the order is generally limited. In the carbon atoms having the sp2-orbital (C—sp2), for example, the valence is four while the number of the hybrid orbitals is three. Thus, the carbon atom includes two single bonds and one double bond as represented by the combination (1, 1, 2), where "1" represents the single bond and "2" represents the double bond. It should be noted that the sum of the numerals in the bracket (1, 1, 2) provides a value 4, which is equal to the valence of carbon.

When two carbon atoms having the state C—sp2 are bonded each other, the order of the bond can either be one or two and the order of the bond is not determined uniquely. However, when oxygen-carbonyl having the number of valence of two and including one single hybrid orbital is bonded to the C—sp2 atom, the order of the hybrid bond that is formed between the C—sp2 atom and the oxygen-carbo-nyl, is determined uniquely to the value two. Thereby, the rest of the hybrid bonds in the C—sp2 carbon are all determined to be one. It should be noted that the oxygen carbonyl has the order of bond of two. Thereby, the order of bond in the C—sp2 atom is determined uniquely when the atomic component representing the oxygen-carbonyl is attached to the structure that includes two atomic component of C—sp2. Generally, it is possible to determine the order of bond uniquely when attaching a atomic component to an existing structural component.

Further, the present invention is not limited to the embodiments described heretofore, but various variations and modifications may be made without departing from the scope of the invention.

What is claimed is:

1. A molecular design support system for creating and/or modifying a molecular structure, comprising:

display means supplied with molecular data representing a molecular structure for displaying said molecular structure graphically;

database means for storing information about atoms forming a molecule in terms of atomic component information, said atomic component information representing information about atomic components that are assembled to form a molecular structure of said molecule, each of said atomic components including an atom and at least one orbital associated therewith, said atomic component information comprising, for each of said atomic components, atomic data and bond data, said atomic data comprising: first identification data for identifying the atomic type of said atom that forms a first atomic component, first coordinate data representing the position of said atom that forms said first atomic component; number data representing the number of the orbitals associated with said atom that form said first atomic component; and second coordinate data showing the position of a free end of the orbital for each of said orbitals in said first atomic component; said bond data comprising: second identification data for identifying the atomic type of an atom that forms a second atomic component and is bonded to the free end of said orbital in said first atomic component; third identification data for identifying the orbital associated with said atom that forms said second atomic component; and fourth identification data for identifying the bond order of a bond that is established between the atoms that respectively form said first and second atomic components;

inputting means including a mouse for selecting the first atomic component, which is initially located at a first position, and moving the first atomic component to a second position, the first atomic component being selected by depressing a mouse button when a mouse cursor is located in the first position, the first atomic component being moved by releasing the mouse button when the mouse cursor is located in the second position; and processing means for manipulating said atomic component information of said first atomic component at said second position to assemble a molecular structure from said first atomic component located at said second position and said second atomic component which is also located at said second position, said processing means producing thereby said molecular data in correspondence to said assembled molecular structure, said processing means including translation means for translating the first coordinate data of the first atomic component to the second position; and rotation means for rotating said first atomic component such that the free end of an orbital in said first atomic component aligns with the orbital that is identified by said third identification data and associated with the atom that forms the second atomic component, said translation means and said rotation means establishing the bond between the atoms that respectively form said first and second atomic components, the bond being formed at said free end of said orbital of said first atomic component and said free end of said orbital of said second atomic component, with a bond order specified by said fourth identification data.

2. A molecular design support system as claimed in claim 1, wherein said processing means includes graphical user interface means for controlling said display means to display a list of said atomic components graphically, said graphical user interface means being manipulated by an operator for selecting an atomic component from said list and for moving said selected atomic component for processing, said graphical user interface means further modifying said molecular data in response to a manipulation by said operator.

3. A molecular design support system as claimed in claim 2, wherein said graphical user interface means is used for specifying a free end of said orbital of said first atomic component and a free end of said orbital of said second atomic component, and wherein said translating means moves said first atomic component according to a translational vector that extends from said free end of said orbital the first atomic component to said free end of said orbital of said second atomic component.

4. A molecular design support system as claimed in claim 3, wherein said rotational means rotates said first atomic component with respect to said second atomic component such that a vector extending from an atom forming said first atomic component to said free end of said orbital of said first atomic component becomes parallel to a vector that extends from an atom forming said second atomic component to said free end of said orbital of said second atomic component.

5. A molecular design support system as claimed in claim 4, wherein said molecular design support system further includes twisting means for twisting said first atomic component with respect to said second atomic component about an axis coincident to a bond that is formed by said orbitals of said first and second atomic components.

6. A molecular design support system as claimed in claim 1, wherein said atomic component information includes, for each of said atomic components, the number of valence of said atom that forms said atomic component, and wherein said processing means determines the order that is formed between said atomic components, upon assembling of said molecular structure.

* * * * *

UNITED STATES PATENT AND TRADEMARK OFFICE
CERTIFICATE OF CORRECTION

PATENT NO. : 5,572,439
DATED : November 5, 1996
INVENTOR(S) : Kazuhiro NISHIDA et al.

It is certified that error appears in the above-indentified patent and that said Letters Patent is hereby corrected as shown below:

<u>Title Page</u>, Item [75], change "Chikushino" to --Fukuoka--.

<u>ABSTRACT</u>, Item [57], line 6, after "components." insert --The atomic component information represents information about atomic components that are assembled to form a molecular structure, and each of the atomic components includes an atom and at least one orbital associated therewith.--

<u>Col. 1</u>, line 7, delete "MOLECULAR DESIGN SUPPORT SYSTEM"

<u>Col. 5</u>, line 14, change "ill" to --in--.

UNITED STATES PATENT AND TRADEMARK OFFICE
CERTIFICATE OF CORRECTION

PATENT NO. : 5,572,439
DATED : November 5, 1996
INVENTOR(S) : Kazuhiro NISHIDA et al.

It is certified that error appears in the above-indentified patent and that said Letters Patent is hereby corrected as shown below:

Col. 6, line 33, change "$b_2$is" to --$b_2$ is--.

Col. 7, line 57, change "8" to --$\theta$--.

Col. 8, line 8, change "x" to --1--.

Col. 9, line 8, change "he" to --the--.

Signed and Sealed this

Twenty-fifth Day of February, 1997

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,572,439
DATED : November 5, 1996
INVENTOR(S) : Kazuhiro NISHIDA et al.

It is certified that error appears in the above-indentified patent and that said Letters Patent is hereby corrected as shown below:

<u>Title Page</u>, Item [22], change "May 22, 1996" to --May 22, 1995--.

Signed and Sealed this

Twenty-second Day of April, 1997

Attest:

BRUCE LEHMAN

*Commissioner of Patents and Trademarks*

*Attesting Officer*